United States Patent [19]
Willy et al.

[11] 3,966,969
[45] June 29, 1976

[54] SPIDER MITE CONTROL
[75] Inventors: William E. Willy; Clive A. Henrick, both of Palo Alto, Calif.
[73] Assignee: Zoecon Corporation, Palo Alto, Calif.
[22] Filed: Mar. 6, 1975
[21] Appl. No.: 555,758

[52] U.S. Cl. .............................................. 424/343
[51] Int. Cl.² ......................................... A01N 9/24
[58] Field of Search .................................. 424/343

[56] References Cited
UNITED STATES PATENTS
3,578,685  5/1971  Archer ............................. 260/396

OTHER PUBLICATIONS
Slama, Annual Review of Biochemistry, (1971), pp. 1079, 1096 and 1097.
Fontaine et al., Chem. Abst. vol. 59, (1963), p. 9822.

*Primary Examiner*—Sam Rosen
*Assistant Examiner*—Allen J. Robinson
*Attorney, Agent, or Firm*—Donald W. Erickson

[57] ABSTRACT

Cyclopropyl substituted alcohols are useful for the control of spider mites.

5 Claims, No Drawings

SPIDER MITE CONTROL

This invention relates to the use of cyclopropyl substituted alcohols for the control of spider mites.

It has now been found that alcohols of Formula I are useful for the control of spider mites.

  (I)

wherein $n$ is an odd integer between 7 and 15.

The compounds of Formula I can be applied to the spider mite at all stages of its development, namely during the egg, larvae, nymphal, and adult stages, thereby causing inability to pass from one stage to the next or inability to reproduce.

A compound of formula I, or mixtures thereof, can be applied at dosage levels of the order of 0.001% to 1%. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound is employed, although higher concentrations of the active compound can be used depending on the type of application and effectiveness of the active ingredient.

The alcohols of formula I are prepared by treating the corresponding acid with a reducing agent such as diborane or the corresponding ester with e.g. sodium diethylaluminum hydride. The preparation of the starting acids is shown in U.S. Pat. No. 3,578,685 and co-pending Ser. No. 489,207, filed July 17, 1974, the disclosure of which is hereby incorporated by reference.

The alcohols of the present invention can be used alone or in an inert carrier substance for the control of mites (Acarina) or can be used in a mixture with pesticides, miticides, especially adulticides and/or juvenile hormone analogs known in the art in order to obtain a broader spectrum of activity. Suitable miticides and insecticides include Plictran, Omite, Baygon, Captan, Sevin, Ciodrin, Systox, Diazinon, Vapona, Galecron, Cygon, Dimethrin, Dursban, Malathion, and Parathion. Typical juvenile hormone analogs which can be used in mixture with the compound of the present invention are described in U.S. Pat. Nos. 3,752,843 and 3,755,411.

The following examples are provided to illustrate the synthesis of the alcohols of this invention and the practice of this invention. Temperature is in degrees Centigrade. Boiling points were measured by short-path distillation.

EXAMPLE 1

To a solution of 2.48 ml. of a 2.55 M solution of sodium diethylaluminum hydride in 10 ml. toluene under nitrogen is added, at 0°, a solution of 1.22 g. methyl 9-cyclopropylnonanoate in 8 ml. toluene. The reaction mixture is allowed to warm to room temperature and is stirred overnight. An additional 3 ml. of the sodium diethylaluminum hydride is added and the reaction mixture is stirred for 2 hours. To the reaction mixture is added, dropwise, 2N sulfuric acid until gas evolution ceases. The mixture is then taken up in ether/2N sulfuric acid, the ether layer is separated and the aqueous phase is extracted twice with 100 ml. ether. The combined ethereal phases are washed in turn with 50 ml. saturated aqueous ammonium chloride and 50 ml. saturated aqueous sodium chloride, dried over calcium sulfate and the solvent removed by evaporation to yield 0.95 g. 9-cyclopropyl-1-nonanol, b.p. 85° at 0.25 mm.

Following the above procedure, the esters of column I are reduced to the corresponding alcohols of column II.

I methyl 7-cyclopropylheptanoate
methyl 11-cyclopropylundecanoate
methyl 13-cyclopropyltridecanoate
methyl 15-cyclopropylpentadecanoate

II 7-cyclopropyl-1-heptanol
11-cyclopropyl-1-undecanol
13-cyclopropyl-1-tridecanol
15-cyclopropyl-1-pentadecanol The miticidal activity of the alcohols of this invention is illustrated by the following test:

Adult mites (*Tetranychus urticae*) were allowed to oviposit for 24 hours on the upper side of lima bean leaf discs (1 cm.) on moist cotton wool. After 24 hours, the adults were removed and the leaf discs were then dipped in acetone solutions of the compound to be tested. After submersion for about one second, the solvent on the leaf discs is allowed to evaporate and the leaf discs are then glued to a plastic petri dish to prevent crumpling. Five days later, the number of unhatched eggs (mortality) is calculated as a percentage of the total number originally present, corrected for any spontaneous non-emergence observed in control discs treated only with solvent (Abbott correction).

Table I presents the results of this miticidal testing:

Table I

| Compound | % concentration in solution | % hatching prevented |
|---|---|---|
| 7-cyclopropyl-1-heptanol | 0.1 | 82 |
| 9-cyclopropyl-1-nonanol | 0.1 | 94 |
| 11-cyclopropyl-1-undecanol | 0.1 | 100 |

A wettable powder suitable for field application after dilution can be formulated by blending and then air-milling a mixture of 20 to 30% of an alcohol of this invention, 60 to 70% of a solid carrier such as Attaclay X-250, 1 to 3% of an anionic surfactant, such as Igepon T-77, and 3 to 5% of a dispersing agent such as Marasperse N-22.

A typical formulation is as follows:

| | |
|---|---|
| 11-cyclopropyl-1-undecanol | 25.0% |
| Synthetic calcium silicate | 40.0% |
| Attapulgite Clay | 29.0% |
| Sodium lignosulfonate | 4.0% |
| Sodium N-methyl N-oleoyl taurate | 2.0% |

What is claimed is:

1. A method for controlling spider mites which comprises applying to the eggs of the spider mite, an ovicidally effective amount of a compound of the formula:

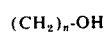-OH wherein n is an odd integer from 7 to 15.

2. The method according to claim 1 wherein n is 9, 11 or 13.

3. The method according to claim 1 wherein the compound is 11-cyclopropyl-1-undecanol.

4. The method according to claim 1 wherein the compound is 9-cyclopropyl-1-nonanol.

5. The method according to claim 1 wherein the compound is 7-cyclopropyl-1-heptanol.

* * * * *

UNITED STATES PATENT OFFICE
CERTIFICATE OF CORRECTION

Patent No. 3,966,969  Dated June 29, 1976

Inventor(s) William E. Willy; Clive A. Henrick

It is certified that error appears in the above-identified patent and that said Letters Patent are hereby corrected as shown below:

Claim 1, the formula reading "$(CH_2)_n$-OH" should read -- $\triangleright\text{-}(CH_2)_n\text{-OH}$ --.

Signed and Sealed this

Twenty-sixth Day of October 1976

[SEAL]

*Attest:*

RUTH C. MASON
*Attesting Officer*

C. MARSHALL DANN
*Commissioner of Patents and Trademarks*